United States Patent
Lott et al.

(10) Patent No.: US 9,281,093 B2
(45) Date of Patent: Mar. 8, 2016

(54) OPERATING PROCESS FOR AN IRRADIATION DEVICE

(71) Applicant: Heraeus Noblelight GmbH, Hanau (DE)

(72) Inventors: Josef Zoltan Lott, Hamburg (DE); Karl-Wilhelm Brieden, Freigericht (DE); Silke Schloemp, Gelnhausen (DE)

(73) Assignee: Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 14/621,624

(22) Filed: Feb. 13, 2015

(65) Prior Publication Data
US 2015/0235727 A1     Aug. 20, 2015

(30) Foreign Application Priority Data

Feb. 17, 2014   (DE) .......................... 10 2014 101 935

(51) Int. Cl.
| | |
|---|---|
| *G21K 5/10* | (2006.01) |
| *H01L 21/263* | (2006.01) |
| *H01L 21/324* | (2006.01) |
| *B41F 23/04* | (2006.01) |

(52) U.S. Cl.
CPC .............. *G21K 5/10* (2013.01); *B41F 23/0409* (2013.01); *H01L 21/263* (2013.01); *H01L 21/324* (2013.01)

(58) Field of Classification Search
CPC ..... B41F 23/0409; G21K 5/10; H01L 21/263; H01L 21/324; H01L 21/67115; B05D 3/0263; B05D 3/06
USPC ................. 250/454.11; 438/795; 156/244.17; 427/314, 557
See application file for complete search history.

(56) References Cited

U.S. PATENT DOCUMENTS

| | | | | | |
|---|---|---|---|---|---|
| 5,832,833 | A | * | 11/1998 | Burgio ................. | B41F 23/044 101/424.1 |
| 6,111,700 | A | * | 8/2000 | Kobayashi ........... | G02B 5/3025 348/E9.027 |
| 6,217,695 | B1 | * | 4/2001 | Goldberg ................ | B05D 3/06 156/244.17 |

(Continued)

FOREIGN PATENT DOCUMENTS

| | | |
|---|---|---|
| DE | 2361415 A1 | 6/1975 |
| JP | H0656132 A | 3/1994 |
| JP | H0794251 B2 | 10/1995 |

OTHER PUBLICATIONS

Office Action issued Oct. 10, 2014 in DE Application No. 10 2014 101 935.0.

*Primary Examiner* — David A Vanore
(74) *Attorney, Agent, or Firm* — Panitch Schwarze Belisario & Nadel LLP

(57) ABSTRACT

Known operating processes for an irradiation device for irradiating a substrate by a UV emitter include the process steps of: (a) operating the UV emitter at a nominal operating radiation power; (b) continuously feeding the substrate at a feed rate into the irradiation field; and (c) irradiating the substrate in the irradiation field defined by the UV emitter. In order to devise, on this basis, a simple and inexpensive operating process for an irradiation device, which makes a short start-up time feasible after an interruption of the production process, the UV emitter is switched off when there is an interruption of the continuous substrate feed. The emitter temperature of the switched-off UV emitter is measured, and provisions are made for counter-measures to counteract a decrease of the emitter temperature by more than 10° C. below the nominal operating temperature.

15 Claims, 4 Drawing Sheets

(56) References Cited

U.S. PATENT DOCUMENTS

| | | | |
|---|---|---|---|
| 7,009,630 B1* | 3/2006 | Finger | B41F 23/0409 347/102 |
| 7,409,777 B2* | 8/2008 | Shiveley | B05D 3/0209 34/275 |
| 9,018,110 B2* | 4/2015 | Stowell | H01L 21/324 438/795 |
| 9,090,114 B1* | 7/2015 | Stumm | B41M 7/0045 |
| 2014/0038431 A1* | 2/2014 | Stowell | H01L 21/324 438/795 |
| 2015/0235727 A1* | 8/2015 | Lott | G21K 5/10 250/454.11 |

* cited by examiner

OPERATING PROCESS FOR AN IRRADIATION DEVICE

BACKGROUND OF THE INVENTION

The invention relates to an irradiation device for irradiating a substrate by a UV emitter, comprising the process steps of:
 (a) operating the UV emitter at a nominal operating radiation power that is a function of a nominal operating temperature;
 (b) continuously feeding the substrate, at a feed rate, into an irradiation field that is defined by the UV emitter; and
 (c) irradiating the substrate in the irradiation field.

Operating processes of this type are often used for operation of irradiation devices in flow-production, for example for disinfection, water reprocessing, or hardening of lacquers, adhesives or plastics.

Known irradiation devices are provided with one or more UV emitters as the radiation source. UV emitters in this spirit include, for example, mercury vapor low pressure lamps, medium pressure lamps, or high pressure lamps. The UV emitter or emitters are arranged appropriately in the irradiation devices, such that they define an irradiation field, in which the substrate is irradiated at a pre-determined minimal irradiation strength. The substrate is fed into the irradiation field by a conveying device, wherein it passes through the irradiation field at constant speed, if possible.

For a given irradiation power of the UV lamp, the residence time of the substrate inside the irradiation field defines the irradiation energy hitting the substrate. A regulation of the conveying rate of the substrate can be used to adapt the irradiation energy hitting the substrate to the ongoing irradiation process.

It is desired, as a matter of principle, to provide for the operation of the irradiation device to be as continuous as possible, i.e. uninterrupted operation, in order to attain good energy efficiency. Upon any interruption of the production process, it must be ensured that a substrate that remains in the irradiation field is not being damaged by excessive irradiation.

To prevent the substrate from being damaged, the UV emitters can be switched off if the production process is interrupted. However, the emitters take a certain time to reach their nominal radiation power again after being switched on. In this context, the radiation power of the UV emitters depends mainly on their temperature. After a cold start, the UV emitter warms up steadily until it reaches its operating temperature. The radiation power stays constant only once the operating temperature is reached. The period of time until the operating temperature is reached is called heating time. Usually, the heating time is on the order of several minutes. Therefore, a re-start of the UV lamp is usually associated with a delay of the production process.

In order to ensure a short heating time after interruption, the prior art refrains from switching-off the UV emitters. Rather, the use of a shielding element interrupting the beam path between UV emitter and substrate is proposed, such that the operation of the UV emitter can be continued even in a standstill of the production process without this having a direct effect on the substrate.

An irradiation device of this type is known from Japanese patent application JP 06-056 132 A. The irradiation device comprises a disinfection lamp that defines an irradiation field, as well as a conveying device that conveys the substrate through the irradiation field. In order to prevent excessive irradiation of a substrate that remains in the irradiation field during a standstill of the irradiation device, the invention of the Japanese publication proposes to arrange, between the UV disinfection lamp and the substrate, a closure door (shutter) that interrupts the beam path between the UV disinfection lamp and the substrate, in the case of a standstill of the production process.

However, the shutter is disadvantageous in that it absorbs some and reflects some of the radiation emitted by the UV emitter, such that it can contribute, in turn, to strong local heating of the surroundings of the UV emitter and thus to heating of the UV emitter. The UV emitter being heated excessively can not only impair its radiation power, but it also contributes to the ageing of the emitter, which is associated with a decrease in the emission in the UV range and a reduced service life of the emitter.

Moreover, continuing operation of the UV emitter during a prolonged standstill is associated with energy being consumed and, often, the substrate to be treated being damaged.

Moreover, the use of a shutter requires the availability of a certain amount of installation space, i.e., sufficient distance between the emitter and the substrate. However, the distance reduces the irradiation strength. As a matter of principle, the irradiation strength attained is largest if the distance between emitter and substrate is as small as possible.

Finally, a shutter is a moving component that needs to be triggered and has a certain susceptibility to failure.

BRIEF SUMMARY OF THE INVENTION

The invention is therefore based on the object of providing a simple and inexpensive operating process for an irradiation device, which circumvents the above-mentioned disadvantages and, concurrently, renders feasible a short start-up time after interruption of the production process.

The object of the invention is met based on an operating process of the type mentioned above in which the UV emitter is switched off if there is an interruption of the continuous substrate feed, wherein the emitter temperature of the switched-off UV emitter is measured, and provisions are made for counter-measures to counteract a decrease of the emitter temperature by more than 10° C. below the nominal operating temperature.

The operating process according to the invention does not include continuous operation of the UV emitter and the use of a shutter. Rather, the invention proposes to switch the emitter off upon any interruption of the substrate feed. Since the operating process according to the invention does not include continuous operation of the UV emitter at operating radiation power, the energy consumption is reduced when there is a standstill of the production process. This enables, on the one hand, a particularly energy-efficient operating process and, on the other hand, prolongs the service life of the emitter.

The disadvantage associated with the shielding element, i.e. excessive heating of the UV emitter upon a standstill of the production process, and the ensuing impairment of the initial radiation power, does not occur in the process according to the invention.

To enable a rapid start-up of the UV emitter and efficient operation of the device after a standstill anyway, further modifications to the operating process are proposed, one of which concerns the monitoring of the emitter temperature after temporary switch-off of the UV emitter and the other of which concerns providing for counter-measures counteracting a decrease of the emitter temperature in the switched-off state.

As a matter of principle, the UV emitter is designed for a pre-determined operating temperature and an operating radiation power, which can be attained by the UV emitter in an optimized production process. In this context, especially the operating temperature of the UV emitter has a significant influence on the radiation power of the UV emitter that can be attained. The operating temperature of the UV emitter being too high or too low is associated with reduced radiation power. The desired radiation power can be set reproducibly particularly well if the UV emitter has virtually the same temperature along its surface.

In order to enable a rapid re-start of a switched-off UV emitter, the invention provides for counter-measures aimed to counteract a decrease in the emitter temperature by more than 10° C. below the nominal operating temperature. For this purpose, the actual temperature of the emitter is determined first and then compared to the nominal operating temperature.

Since the UV emitter is maintained at a temperature close to its operating temperature, the heating time can be short. Since the UV emitter temperature deviates at most by 10° C. from the operating temperature during operation, the UV emitter can reach its operating radiation power within less than 5 seconds.

The operating parameters of the irradiation device are adapted to the operating radiation power of the UV emitter. In the simplest case, the irradiation device is operated at a feed rate that is optimized for the nominal operating radiation power. As a result, the substrate is not only irradiated by sufficient radiation energy, but also the speed of the production process is guaranteed to be as high as possible.

A preferred embodiment of the operating process according to the invention provides for heating of the UV emitter by a heating element as a counter-measure.

In the simplest case, a temperature control unit having a heating element is provided in the vicinity of the UV emitter, for example in the form of an infrared emitter or a heating coil by which the emitter temperature can be maintained in the temperature range about the operating temperature. As a result, the UV emitter can exert its maximal radiation power within a manner of seconds.

An alternative embodiment of the operating process according to the invention that is also preferred provides for the emitter temperature to be influenced by an air flow generated by an air cooling and, as counter-measure, to provide for heating of the air flow by a heating element.

In order to operate the UV emitter at its specific nominal operating temperature, at which the radiation power of the UV emitter is optimized, the invention provides an air cooling for the UV emitter. The air cooling generates a flow of air that flows past the surface of the UV emitter or flows around the surface of the UV emitter and thus exerts an influence on the emitter temperature towards the nominal operating temperature, i.e. decreases or increases the current emitter temperature as the case may be. It has proven to be expedient in this context to have the air flow flow around the surface of the UV emitter.

The emitter temperature can just as well be influenced by adapting the air cooling. Depending on the temperature of the ambient air aspirated by the air cooling, the air cooling allows the emitter surface to be heated or cooled; the air flow can effect either an increase or a decrease of the emitter temperature. An air flow flowing past the UV emitter or around the UV emitter contributes to the UV emitter being heated or cooled as evenly as possible and contributes to preventing excessive local heating of the UV emitter.

Since the heating element heats the air flow, the temperature of the UV emitter can be increased by the air flow and thus can be maintained in the desired temperature range. Moreover, the heated air flow contributes to even heating of the emitter.

Preferably, the heating element is an electrical heating element having a heating coil through which an electrical current flows. A heating element of this type can be manufactured easily and inexpensively and, moreover, it has little inertia, such that the heating power can be set and adapted comparatively easily. Lastly, an electrical heating element of this type is easy to trigger. The heating element is preferred to be a short-wave infrared emitter. The heating power of a short-wave infrared emitter is available very rapidly, such that rapid temperature changes and rapid heating of the UV emitter become feasible.

A further advantageous refinement of the operating process according to the invention provides for the emitter temperature to be influenced by an air flow generated by an air cooling and, as a counter-measure, provides for changing a mass flow of the airflow.

Since the air flow is variable, the emitter temperature can be influenced by a change in the mass flow of the air flow. If, for example, the temperature of the air flow is higher than the emitter temperature, an increase in the mass flow results in the emitter being heated. But if the temperature of the air flow is lower than the emitter temperature, a reduction of the mass flow contributes to keeping the UV emitter warm for as long as possible.

The air flow of the air cooling allows the emitter temperature to be accurately set, even during the operation, of the irradiation device, and contributes to the emitter temperature staying even.

In the ease of the continuous substrate feed being interrupted, it has proven expedient
 (aa) to switch the UV emitter off; and
 (bb) to switch the heating element on;
and when the interruption of the continuous substrate feed is no longer present
 (cc) to switch the UV emitter on; and
 (dd) to switch the heating element off.

Switching the emitter off and switching the heating element on when the production process is interrupted, maintains the emitter temperature in a temperature range about the operating temperature during the interruption. Therefore, the emitter reaches a high radiation power right after the production process is re-started. In this context, it has proven to be expedient, to switch the UV emitter on and, concurrently, to switch the heating element off. The heating element being switched off concurrently contributes to preventing excessive heating of the UV emitter at operating conditions.

It has proven expedient to heat the air flow in an air feed channel of the air cooling. Having the heating element arranged in an air feed channel is advantageous in that tine air can be heated in close proximity to the UV emitter, such that a particularly energy-efficient operating process is made feasible. Concurrently, this counteracts uneven heating of the UV emitter.

A preferred refinement of the process according to the invention provides the irradiation device with a reflector having a side facing the UV emitter and a side facing away from the UV emitter, and provides the air flow to be heated by a heating element arranged on the side of the reflector facing away.

The reflector is firmly connected to the UV emitter or the reflector is a separately arranged reflector component that has a side facing the UV emitter and a side facing away from the UV emitter.

Since the heating element is arranged downstream of the reflector, i.e. on the side facing away from the UV emitter, the UV emitter heats just the reflector directly. Since the UV emitter is not exposed to any direct heating by the heating element and is heated, at most, indirectly via the reflector, uneven and local heating of the UV emitter is prevented. The arrangement therefore contributes to the UV emitter being heated evenly.

Preferably, the air flow flows around the UV emitter in a direction perpendicular to the longitudinal direction of the emitter. This facilitates even heating of the UV emitter.

It has proven expedient to consecutively detect the feed rate with a sensor. Efficient adaptation of the radiation power of the UV emitter to the feed rate is made feasible if the feed rate is determined consecutively—i.e. continuously or from time to time. The sensor provided for determination of the feed rate can detect the feed rate, for example, by detecting an electrical or optical measuring parameter. Preferably, the feed rate is measured in a contact-less manner through the use of an optical correlation measuring system, for example by a camera.

It has proven expedient to consecutively detect the temperature of the UV emitter with a sensor. The temperature sensor converts the temperature into an electrical measuring parameter. It detects the temperature of the UV emitter consecutively, i.e. continuously or from time to time. Referring, in particular, to the concurrent use of multiple UV emitters, each of the emitters can be provided with a temperature sensor. Alternatively, the temperature can be detected just on a single emitter or on individual emitters. The temperature is preferably detected on the surface of the emitter tube. Detecting the emitter temperature consecutively facilitates the earliest possible detection of deviations of the emitter temperature from a given nominal value. This provides for a particularly dynamic operating process.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred, it should be understood, however, that the invention is not limited to the precise arrangements and instrumentalities shown. In the drawings.

DETAILED DESCRIPTION OF THE INVENTION

Figure 1:
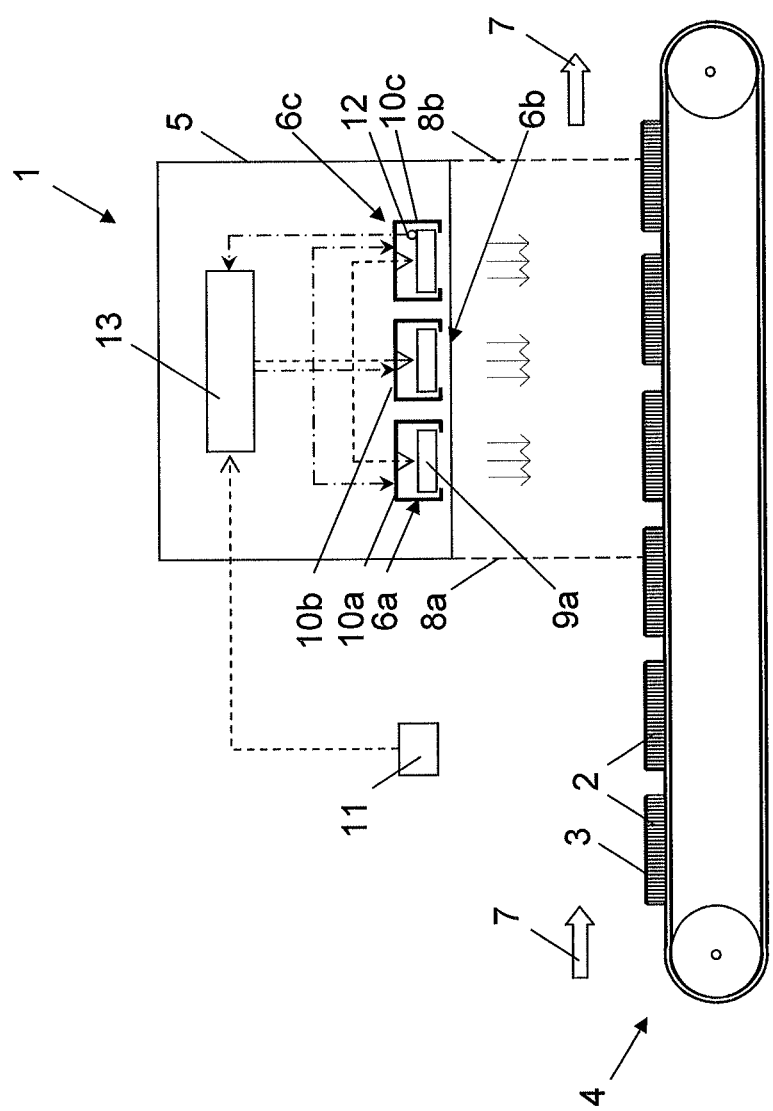
FIG. 1 is a schematic side elevation view of an embodiment of an irradiation device for irradiation of a substrate working according to the operating process of the invention.

FIG. 1 is a schematic view of an embodiment, of an irradiation device working according to the inventive operating process, which overall has reference number 1 assigned to it. The irradiation device 1 is used for cross-linking and curing a coating 3 on work-pieces 2 in the form of plastic films.

The irradiation device 1 comprises an emitter unit 5 for irradiation of the work-pieces 2 and a conveying device 4 feeding the work-pieces 2 continuously in the conveying direction 7 for irradiation by the emitter unit 5.

The emitter unit 5 comprises three emitter modules 6a, 6b, 6c, arranged in series, as well as a control unit 13 for the emitter modules 6a, 6b, 6c. The emitter modules 6a, 6b, 6c are provided to be identical in design. Therefore, only emitter module 6a is described in more detail below.

The emitter module 6a comprises a UV emitter 9a to which a heating element 10a for heating of the UV emitter 9a is assigned. The UV emitter 9a comprises a cylindrical emitter tube made of quartz glass and has a longitudinal axis of the emitter tube. It is characterized by a nominal power of 300 W and a length of the emitter tube of 1,000 mm.

The emitter modules 6a, 6b, 6c are arranged inside the emitter unit 5 and with respect to the conveying device 4 in appropriate manner, such that the longitudinal axes of the emitter tubes extend perpendicular to the conveying direction 7. The emitter unit 5 defines on the surface of the conveying device 4 an irradiation field for irradiation of the work-pieces 2. The extension of the irradiation field in the conveying direction 7 is drawn as dashed lines 8a, 8b in FIG. 1.

The conveying device 4 moves the work-pieces 2 with respect to the emitter unit 5, such that these slowly pass through the irradiation field. The distance between the emitter unit 5 and the surface of the work-pieces 2 is 20 mm and can be adjusted by a device for distance adjustment (not shown).

The irradiation device 1 is based on the operating process according to the invention. Before the work-pieces 2 are fed into the irradiation field of the emitter unit 5, the UV emitters 9a, 9b, 9c are switched on, such that they can reach their operating temperature. An alternative refinement of the operating process provides for the UV emitters in each be pre-heated and/or maintained constantly at operating temperature by the corresponding heating element 10a, 10b, 10c, and started-up subsequently.

Once the UV emitters 9a, 9b, 9c reach their pre-determined operating temperature and operating radiation power, the conveying device 4 feeds the work-pieces 2 into the irradiation field at a pre-determined conveying rate. To enable efficient operation of the irradiation device 1, the conveying rate is adapted to the mean operating radiation power of the UV emitters 9a, 9b, 9c. In this context, the work-pieces 2 pass through the irradiation field at a conveying rate that is as close to constant as possible. The conveying rate is detected continuously by an optical sensor 11 that determines the travel of a work-piece 2 in a pre-determined time interval. The sensor 11 continuously transmits the conveying rate to the control unit 13 of the emitter unit 5.

If the production process comes to a standstill while the process is ongoing, there is a risk that the work-pieces 2 situated in the irradiation field might be exposed to UV irradiation for too long and might thus be damaged. In order to prevent this from occurring, the invention provides the operating parameters of the emitter modules 6a, 6b, 6c to be controlled as a function of the conveying rate by the control unit 13. The emitter modules 6a, 6b, 6c are switched off upon a production standstill.

In order to ensure that the irradiation of the work-pieces 2 at a high irradiation power resumes with as little delay as possible once production starts-up again, the temperature of the UV emitters 9a, 9b, 9c is measured concurrently. For detection of the emitter temperature, a temperature sensor 12 is arranged on the emitter tube of the UV emitter 9c of emitter module 6c and detects the actual temperature of the emitter tube. In an alternative embodiment (not shown), each emitter module 6a, 6b, 6c is provided with a temperature sensor 12. If the temperature of the UV emitter 9a, 9b, 9c decreases by more than 10° C. below the operating temperature thereof, the control unit 13 switches the corresponding heating element 10a, 10b, 10c on such as to heat the air flow flowing around the UV emitter in a direction perpendicular to the longitudinal direction of the emitter. The UV emitters 9a, 9b, 9c are thus maintained at a temperature in the range of their operating temperature during the production standstill.

Maintaining the UV emitter 9a, 9b, 9c at operating temperature reduces the time needed by the UV emitter 9a, 9b, 9c at a re-start to reach its operating radiation power. As a result, an immediate start-up of the irradiation device 1 at a high conveying rate is made feasible after a standstill. Upon the production re-start, the heating element 10a, 10b, 10c is switched off concurrently when the UV emitter 9a, 9b, 9c is switched on again.

Figure 2:
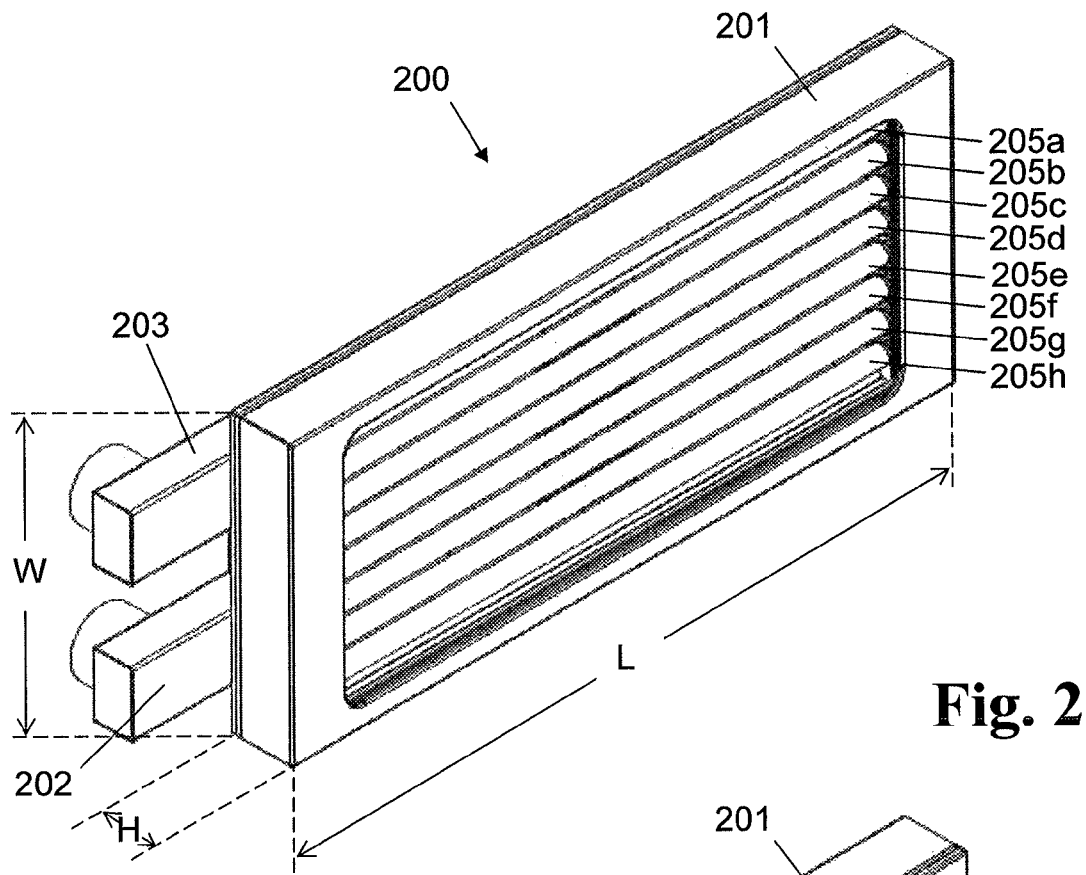
FIG. 2 is a front perspective view of a first emitter module for use in the irradiation device according to FIG. 1, in which a heating coil is arranged in an air feed channel.

FIG. 2 schematically shows a front view of an emitter module 290, which can be inserted into the irradiation device according to FIG. 1.

The emitter module 200 comprises a housing 201 that has eight UV emitters 205a-205h arranged in it. The housing 201 is made of stainless steel, it has a length L of 1,030 mm, a width B of 434 mm, and a height H of 171 mm. Ventilation channels 202, 203 are arranged on the rear of the housing 201.

The UV emitters 205a-205h each comprise a cylindrical emitter tube made of quartz glass, which is closed on both ends and comprises a longitudinal axis of the emitter tube. The characteristic parameters of the UV emitters 205a-205h are the nominal power of 300 W (at a nominal lamp current of 4 A), an emitter tube length of 100 cm, an emitter tube outer diameter of 28 mm, and a power density of 3 W/cm. The emitters are arranged appropriately inside the housing, such that the longitudinal axes of the emitter tubes extend parallel to each other.

Figure 3:
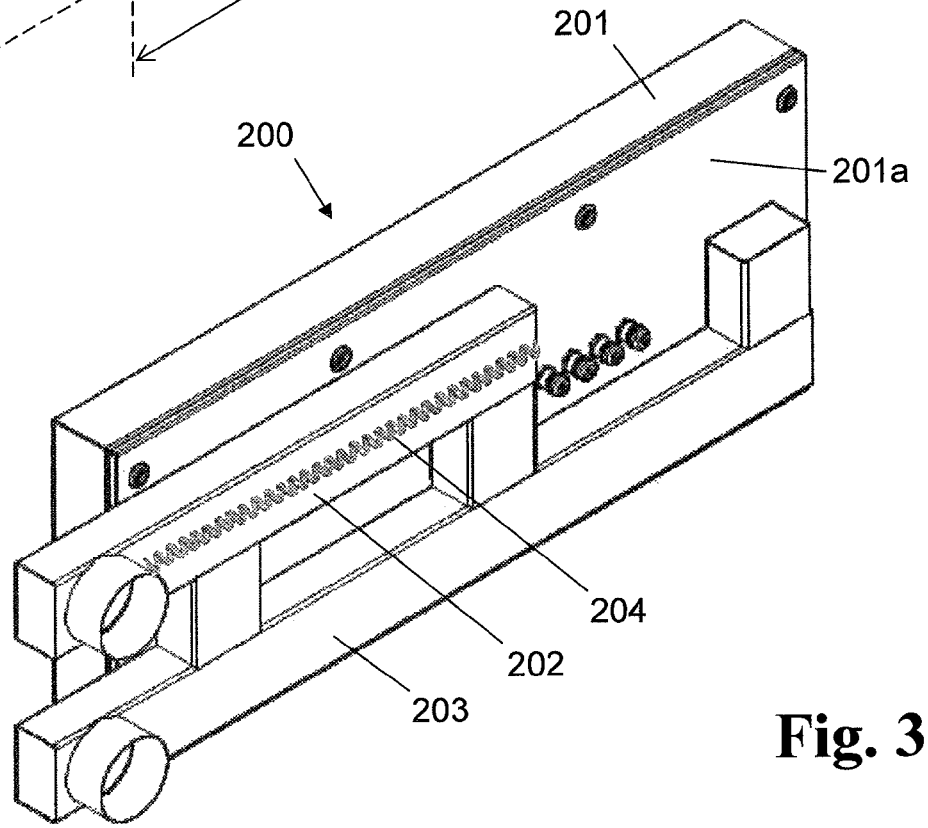
FIG. 3 is a rear perspective view of the emitter module according to FIG. 2.

FIG. 3 schematically shows a rear view of the emitter module 200 for use in the irradiation device according to FIG. 1. The emitter module 200 comprises a housing 201, which has eight UV emitters 205a-205h arranged in it (not visible in the drawing). Ventilation channels 202, 203 are arranged on the rear 201a of the housing 201 and can be used to cool the UV emitters during operation by an air flow that flows towards the emitters in a direction perpendicular to the longitudinal direction of the emitters. The ventilation channel 202 is an air feed channel, whereas the ventilation channel 203 is used as a discharge channel. A heating coil 204 is arranged in the ventilation channel 202.

If the emitter module 200 is operated at nominal power, the UV emitters 205a-205h incorporated into the emitter module 200 are heated up. To prevent excessive heating of the UV emitters 205a-205h and the housing 202 and to be able to operate the UV emitters 205a-205h at optimized radiation power, the emitters 205a-205h can be exposed to a flow of cooling air and thus can be cooled by the ventilation channel 202. In this context, the cooling air warmed up by the emitters 205a-205h is discharged through the discharge channel 203. The air flow is variable meaning, in particular, that the mass flow of the air flow can be adapted in order to adapt the cooling power.

To prevent the switched-off UV emitters 205a-205h from cooling down, a heating element 204 is arranged in the air feed channel 202 and can be switched on according to need. The heating element 204 serves for heating the air supplied through the air feed channel 202, which in turn, contributes to heating the UV emitters 205a-205h. Controlling the air feed temperature allows the UV emitters 205a-205h to be maintained at operating temperature.

Figure 4:
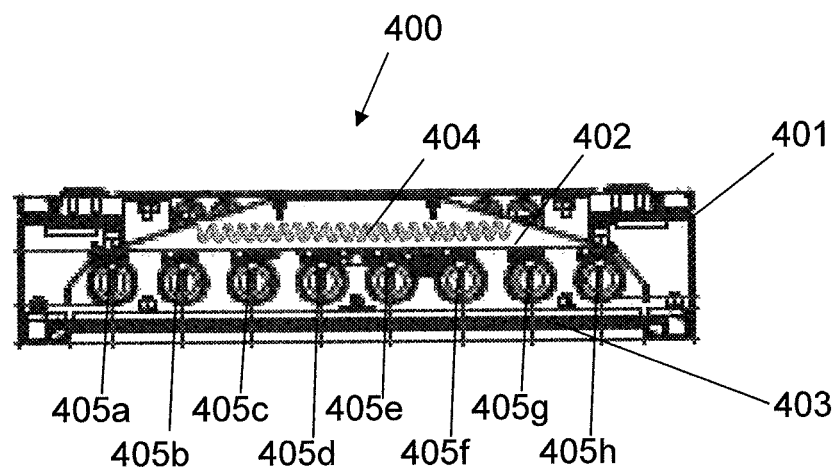
FIG. 4 is a schematic cross-sectional view of a second emitter module for use in the irradiation device according to FIG. 1, in which a heating element extending perpendicular to the longitudinal direction of the emitter module is arranged downstream of a reflector.

FIG. 4 schematically shows a cross-sectional view of a second embodiment of an emitter module for use in the irradiation device according to FIG. 1. The emitter module overall has reference number 400 assigned to it. The dimensions of the emitter module 400 are given in FIG. 1 in units of mm. The emitter module 400 comprises a housing 401 having eight UV emitters 205a-205h arranged in it, and a housing window 403 made of quartz glass. Moreover, a reflector 402 made of aluminum is arranged on the inside of the emitter module 400. In contrast to the emitter module 200 from FIGS. 2 and 3, the emitter module 400 does not have air cooling. Moreover, a heating element 404 is arranged downstream of the reflector 402 and heats the reflector 402 and therefore, indirectly, the UV emitters 405a-405h as well. In this context, the heating element 404 extends perpendicular to the longitudinal axis of the emitter module 400. Viewed in the direction of the longitudinal axis, four heating elements are arranged parallel with respect to each other (not shown).

Figure 5:
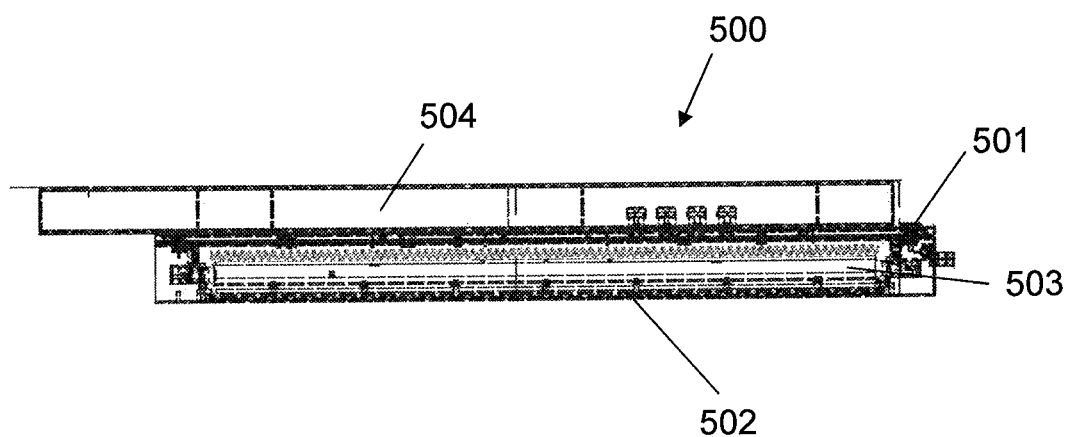
FIG. 5 is a schematic longitudinal view of a third emitter module for use in the irradiation device according to FIG. 3, in which a heating coil extending in the longitudinal direction of the emitter module is arranged downstream of a reflector.

FIG. 5 shows a schematic view of a third embodiment of an emitter module, which overall has reference number 500 assigned to it. The emitter module 500 comprises a housing 501 having four UV emitters 503 arranged in it and has an air cooling system 504 for cooling the UV emitters 503 attached to its rear. An ultraviolet radiation-translucent window 502 made of quartz glass is fitted into the front of the housing 501. A heating element is arranged between the rear-side wall of the housing 501 and the UV emitters 503 and extends parallel to the longitudinal axis of the UV emitters 503.

Figure 6:
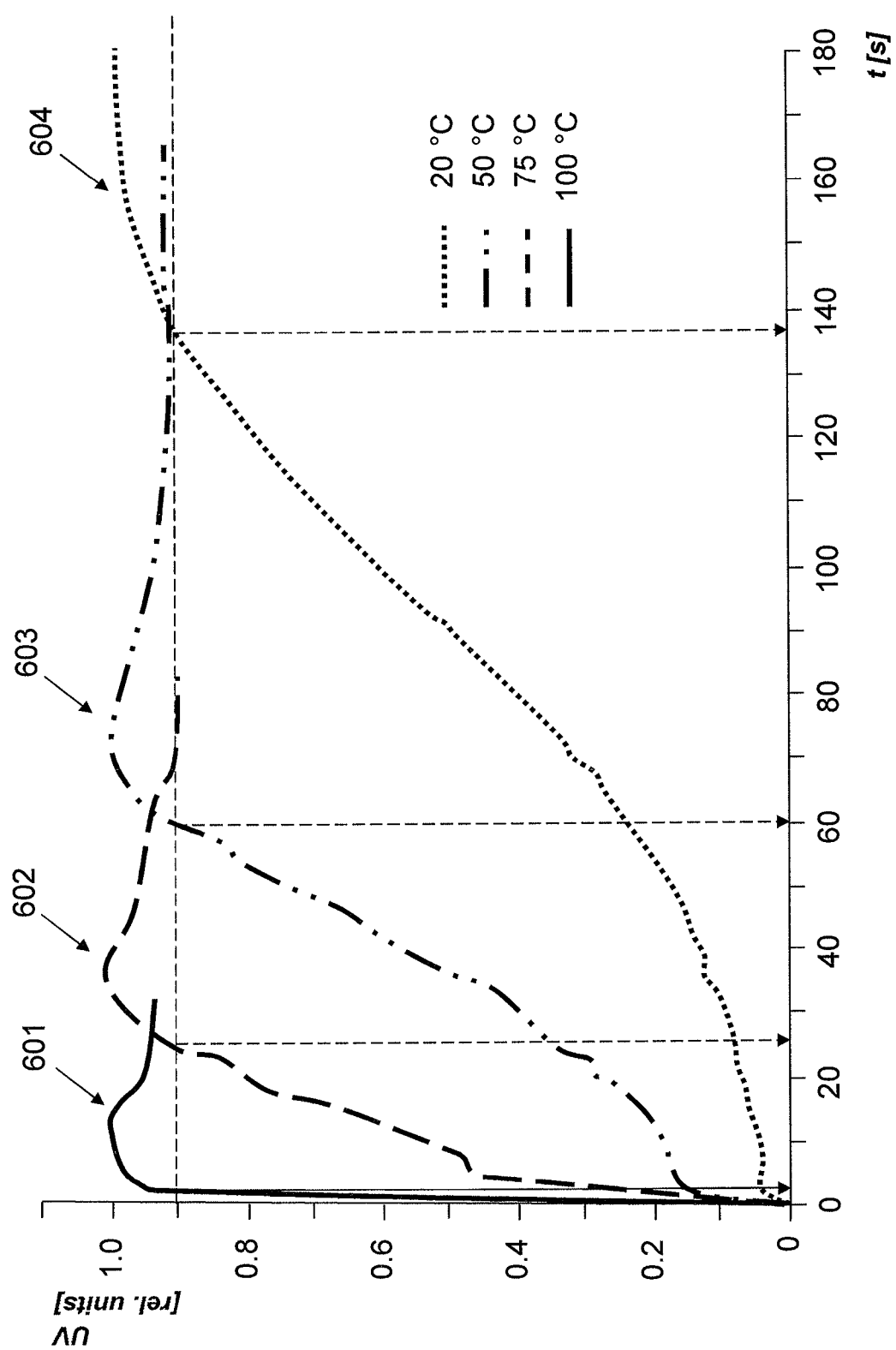
FIG. 6 is a graphical diagram in which the relative UV emission of a UV emitter operated according to the inventive process is shown as a function of the time elapsed (in seconds) since start-up of the emitter for differently pre-heated emitters.

The diagram in FIG. 6 shows the UV emission of a UV emitter at a wavelength of 254 nm as a function of the time elapsed after start-up of the UV emitter for various emitter start-up temperatures.

A low-pressure emitter having an emitter tube made of quartz glass and closed on both ends by crimpings was used as the UV emitter. The emitter tube of the low-pressure emitter encloses an argon-filled discharge space, in which an amalgam reservoir and two electrodes are arranged.

The characteristic parameters of the low-pressure emitter are its nominal power of 300 W (at a nominal lamp current of 4 A), an emitter tube length of 100 cm, an emitter tube outer diameter of 28 mm, and a power density of 3 W/cm.

The low-pressure emitter was first heated to a start-up temperature before starting it up. For this purpose, the temperature of the low-pressure emitter was determined in the middle of the emitter tube using a temperature sensor attached to the outside of the emitter tube. The selected start-up temperatures were 20° C., 50° C., 75° C., and 100° C. Subsequently, the low-pressure emitter was started up at time t=0. FIG. 6 shows a profile of the UV emission as a function of the time elapsed after start-up for each of these start-up temperatures. The time elapsed since start-up of the emitter is plotted on the abscissa in units of seconds. The ordinate reflects the emission of ultraviolet radiation in relative units.

For the UV emission power to be good, the low-pressure emitter must be at a certain temperature. Since the low-pressure emitter heats up during operation, the temperature is attained after a certain time of operation. As is evident from the curve profile 604, an emitter that had been pre-heated to a temperature of 20° C. reaches an acceptable UV emission after approx. 135 s. The time to an acceptable UV emission can be attained by pre-heating the emitter tube. According to curve profile 603, a start-up temperature of 50° C. leads to a start-up time of approx. 65 s. At a start-up temperature of 75° C., the start-up time is reduced to approx. 23 s, and, in particular, at a start-up temperature of 100° C., a start-up time of less than 5 s can be attained (curve profiles 601, 602).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention, as defined by the appended claims.

We claim:

1. An operating process for an irradiation device for irradiating a substrate by a UV emitter, the process comprising steps of:
    (a) operating the UV emitter at a nominal operating radiation power that is a function of a nominal operating temperature;
    (b) continuously feeding the substrate, at a feed rate, into an irradiation field defined by the UV emitter; and
    (c) irradiating the substrate in the irradiation field,
wherein the UV emitter is switched off if there is an interruption of the continuous substrate feed, wherein an emitter temperature of the switched-off UV emitter is measured, and wherein counter-measures are provided to counteract a decrease of the emitter temperature by more than 10° C. below the nominal operating temperature.

2. The operating process according to claim 1, wherein one of the counter-measures comprises heating the UV emitter by a heating element.

3. The operating process according to claim 1, wherein the emitter temperature is influenced by an air flow generated by air cooling, and wherein one of the counter-measure comprises heating of the air flow by a heating element.

4. The operating process according to claim 1, wherein the emitter temperature is influenced by an air flow generated by air cooling, and wherein one of the counter-measures comprises changing a mass flow of the air flow.

5. The operating process according to claim 2, wherein, if the continuous substrate feed is interrupted,
    (aa) the UV emitter is switched off; and
    (bb) the heating element is switched on;
and when the interruption of the continuous substrate feed is no longer present;
    (cc) the UV emitter is switched on; and
    (dd) the heating element is switched off.

6. The operating process according to claim 3, wherein the air flow is heated in an air feed channel of the air cooling.

7. The operating process according to claim 3, wherein the irradiation device comprises a reflector having a side facing the UV emitter and a side facing away from the UV emitter, and wherein the air flow is heated by a heating element arranged on the side of the reflector facing away from the UV emitter.

8. The operating process according to claim 3, wherein the air flow flows around the UV emitter in a direction perpendicular to a longitudinal extent of the emitter.

9. The operating process according to claim 1, wherein the feed rate is detected consecutively by a sensor.

10. The operating process according to claim 1, wherein the temperature of the UV emitter is detected consecutively by a sensor.

11. The operating process according to claim 3, wherein, if the continuous substrate feed is interrupted,
    (aa) the UV emitter is switched off; and
    (bb) the heating element is switched on;
and when the interruption of the continuous substrate feed is no longer present;
    (cc) the UV emitter is switched on; and
    (dd) the heating element is switched off.

12. The operating process according to claim 6, wherein the irradiation device comprises a reflector having a side facing the UV emitter and a side facing away from the UV emitter, and wherein the air flow is heated by a heating element arranged on the side of the reflector facing away from the UV emitter.

13. The operating process according to claim 4, wherein the air flow flows around the UV emitter in a direction perpendicular to a longitudinal extent of the emitter.

14. The operating process according to claim 6, wherein the air flow flows around the UV emitter in a direction perpendicular to a longitudinal extent of the emitter.

15. The operating process according to claim 7, wherein the air flow flows around the UV emitter in a direction perpendicular to a longitudinal extent of the emitter.

* * * * *